United States Patent [19]

Lazorthes

[11] Patent Number: 4,718,894

[45] Date of Patent: Jan. 12, 1988

[54] MANUALLY ACTUATED, IMPLANTABLE DEVICE TO SEQUENTIALLY FEED DOSES OF A SUBSTANCE, IN PARTICULAR A THERAPEUTANT

[75] Inventor: Guy Lazorthes, Toulouse, France

[73] Assignee: Applied Precision Limited, London, England

[21] Appl. No.: 865,413

[22] Filed: May 21, 1986

[30] Foreign Application Priority Data

May 21, 1985 [FR] France .................................. 85 08068

[51] Int. Cl.⁴ .............................................. A61M 5/00
[52] U.S. Cl. ...................................... 604/93; 604/185; 604/891.1
[58] Field of Search ...................... 604/9, 93, 153, 185, 604/246, 891

[56] References Cited

U.S. PATENT DOCUMENTS

| | | | |
|---|---|---|---|
| 4,548,607 | 10/1985 | Harris | 604/153 X |
| 4,588,394 | 5/1986 | Schulte et al. | 604/9 |

*Primary Examiner*—Dalton L. Truluck
*Attorney, Agent, or Firm*—Harold H. Dutton, Jr.

[57] ABSTRACT

The invention concerns a sequential and manually actuated feed device for implantation in an accessible subcutaneous region of a patient for the purpose of sequentially dosing a liquid, in particular a therapeutant. This device comprises a reservoir consisting of a flexible pouch, a filling site (2) located at the rim of said pouch in order to inject the liquid into it, and a manual pump (3) located in the opposite zone of the pouch in order to supply the liquid dose by dose to a catheter (20). The pump has a rigid case with a recess and bearing an expulsion membrane so as to bound a volume chamber; safety means prevent any accidental injection in the event of a spurious pressure exerted on the flexible pouch.

21 Claims, 9 Drawing Figures

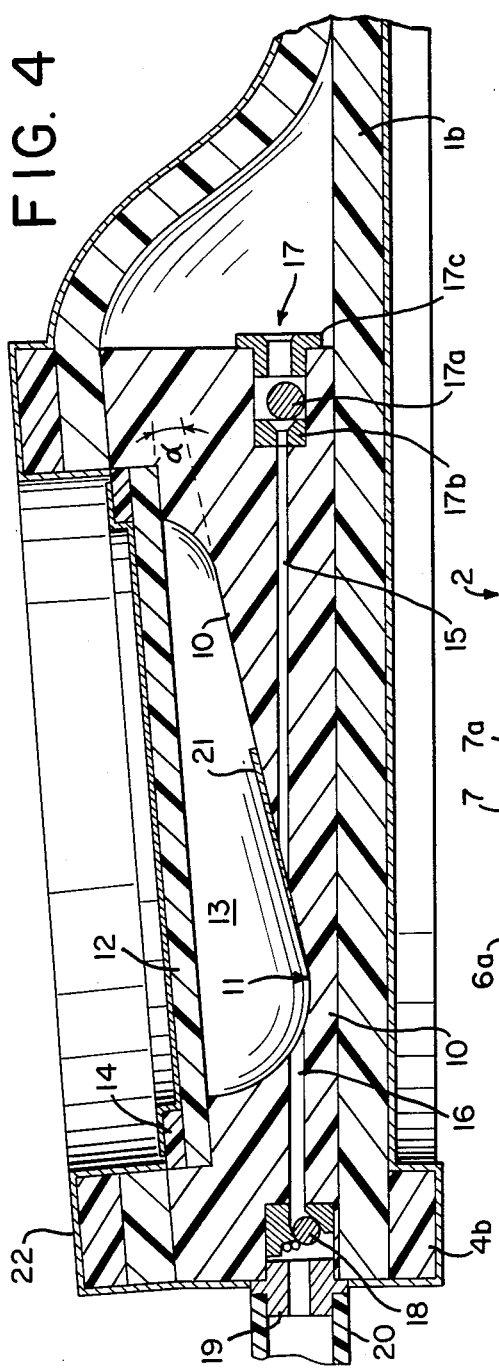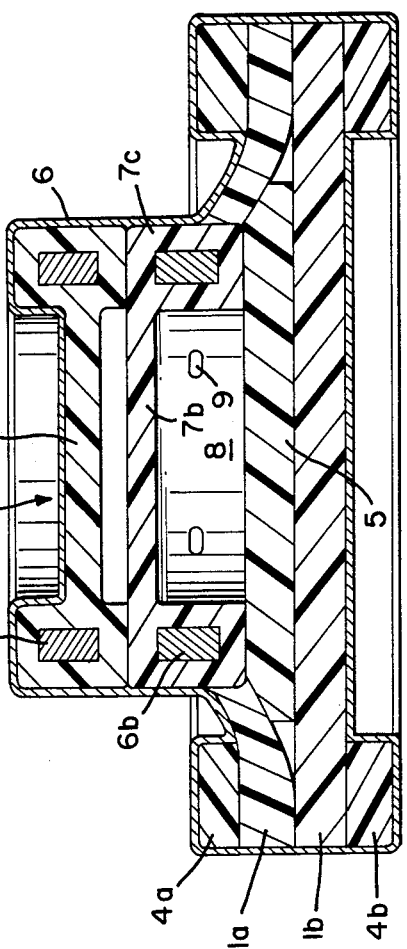

MANUALLY ACTUATED, IMPLANTABLE DEVICE TO SEQUENTIALLY FEED DOSES OF A SUBSTANCE, IN PARTICULAR A THERAPEUTANT

The invention concerns a sequential feeding device intended to be totally implanted in an accessible subcutaneous region of the body of a patient in order to feed liquid doses (essentially therapeutic doses); more particularly the invention relates to a type of device with a reservoir holding several doses, a site refilled through a skin puncture in order to replenish the reservoir, and an injection pump for expelling a dose into a catheter inserted in the body compartment that is to receive the injected liquid.

BACKGROUND AND OBJECTS OF THE INVENTION

Recently many implantable devices of this kind have been provided; they are placed in the course of a surgical procedure beneath the skin tissue so that the refilling site is accessible through the skin, the catheter being implanted between the device and the particular body compartment. In this manner it is possible to selectively feed an accurate dose (also called "embolus") at the desired target with pharmacological concentrations only in that area and with negligible concentrations elsewhere; storing a plurality of emboli makes the device autonomous for several injections.

In some devices the pumps are actuated by automatic means making it possible to program the injections (electromagnetic pumps: French patent No. 2,537,440, WO patent No. 81/00888 . . . ; electric motor pumps: European patent No. 11 25 85, U.S. Pat. No. 4,447,224, French patent No. 2,354,105, European patent No. 2 50 05, thermodynamic or chemical energy pumps: French patent Nos. 2,528,313; 2,370,481; Canadian patent No. 946,696; U.S. Pat. No. 3,731,681; WO patent No. 80/01755, French patent No. 2,195,461, U.S. Pat. No. 3,692,027 . . . ; osmotic or electroosmotic pumps: French patent Nos. 2,390,177 and 2,354,106, U.S. Pat. Nos. 4,340,054, 4,300,557, 3,995,631 . . . ). However these are complex, very costly bulky and often only partly implantable devices.

Furthermore devices are known wherein the pump is manually actuated by the patient himself or the practitioner in order to inject an embolus. Illustratively the U.S. Pat. No. 4,013,074 describes a device of this type which comprises within a rigid enclosure on one hand a liquid reservoir and a gas reservoir separated by a diaphragm and on the other hand a peristaltic pump which can be manually actuated through the skin by means of a suitable mechanical system. The manually actuated devices of this type as a rule are simpler than the automated devices mentioned above; also they allow administering the drug upon demand in a much more flexible manner, which is a significant factor frequently (especially when injecting anti-plan opiates). However the known devices of this kind remain relatively complex and hence costly (for instance because of the presence of moving mechanical members in the case of the above cited device), and as a rule they bother the patient when they are implanted in the tissues, sometimes being difficult to implant or to actuate (some requiring several operations in a predetermined sequence to inject a dose).

The object of the present invention is a novel sequential feed device of the manually actuated kind and intended to be implanted in an accessible subcutaneous region in order to sequentially feed doses or emboli. Essentially the object of the invention is a device with a much simplified structure which is cheaper to produce than the known devices of this type.

Another main object of the invention is to create a device with a reservoir containing an increased number of doses in order to increase its autonomy while retaining a small bulk and a shape proper to ease its implantation.

Another object is to create a device which can be integrated into the subcutaneous tissues by adapting itself to their local shapes in order to reduce the bother suffered by the patient.

Another object is to create a device allowing easy and reliable use and capable to feed upon each pump acutation an exact and predetermined dose.

Another object of the invention is to provide the device with an auxiliary access site for the chronic injection of substances different from that contained in the reservoir (complementary drug administration, sealing check by opaqueproduct injection . . . ).

Another object is to provide a device without any danger of interference or artifacts in the course of modern imaging exploration techniques (tomodensitometry, magnetic resonance . . . ).

DESCRIPTION OF THE INVENTION

To those ends, the device of the invention is of the type which comprises:
  a reservoir with a multi-dose capacity,
  a reservoir filling site with a filling chamber, a liquid injection septum in said chamber and means providing communication between the filling chamber and the reservoir,
  and a manual pump including a volume-chamber with a capacity of one dose, means for communicating between the reservoir and said chamber in order to fill latter, and means for communicating between said volume chamber and an external catheter.

The device of the present invention is characterized in that:
  (a) the reservoir comprises a flexible pouch, having a first flexible and so-called external wall and a second and so-called internal wall, these walls extending opposite one another and being joined impermeably along their rims.
  (b) the manual pump include a rigid integral case which
    when viewed along its thickness has a recess issuing in one side of said body which is called the active side in order to form the volume chamber,
    is placed between the two flexible walls of the pouch forming the reservoir,
    and is fixed by its opposite side to the internal flexible wall,
  (c) the means for communicating between the volume chamber and the catheter are provided with a one-way valve with a pressure threshold which is fitted to allow communication between the chamber and the catheter when the chamber undergoes an excess pressure beyond a predetermined threshold,
  (d) the means for communicating between the reservoir and the volume chamber are provided with:
    a check valve preventing the liquid from flowing back from the chamber into the reservoir, a safety valve fitted to permit gravity flow flow from the reservoir to the volume chamber and to seal the communication if the reservoir excess pressure exceeds a value Pr less than or equal to the threshold Pc.

Preferably the flexible pouch forming the reservoir is stiffened at the rim of its flexible walls by a peripheral frame fastened to the rim of the flexible walls.

In another feature of the invention, the reservoir filling site is located between two flexible walls near their rim and in a zone of the pouch that is opposite the one holding the manual pump; this site includes a ring holding the injection septum which preferably includes two elastic membranes separated by a vacuum (this design achieves a sort of a lock space improving the impermeability of the filling site after a large number of perforations). It is possible too to provide an injection septum by the so-called silicone-plug method.

Accordingly the device of the invention is entirely integrated into a flexible pouch defining its shape and its outer texture. It lacks any mechanical member, the injection taking place directly by a membrane-caused expulsion from a manual pressure exerted on it through the skin of the patient. Such a device has a very simple geometry and its manufacture (in particular by stacking and bonding the diverse constituents, as discussed further below) is very economical compared to the previous products. Furthermore the flexible pouch can easily be inserted into the subcutaneous tissues during implantation. Its flexibility allows it to hug the local tissue shapes with only very little bother for the patient (contrary to the case of the prior art devices with their rigid enclosures). The peripheral frame keeps the pouch in place radially but allows the device to deform perpendicularly to its plane to perfectly integrate into the adjacent tissues. Also, the holding capacity of the reservoir formed by the flexible pouch may be made to correspond to a fairly large number of doses (for instance about 80) because, on one hand, of the very adaptation of said reservoir and on the other hand the negligible space occupied by the other members (pump and filling site). An embolus is injected by a single actuation which can be performed by the patient himself and which comprises forcing the expulsion membrane into the recess of the device body down to its bottom; preferably this recess assumes a shape matching the forefinger. This easily carried out actuation achieves the injection of an accurate dose which corresponds to the space of the volume chamber bounded by the recess. Device operation is highly reliable: in particular, as shall be seen further below, no accidental injection may take place for instance in the event of accidental pressure exerted on the flexible pouch forming the reservoir.

In a preferred embodiment, the flexible pouch forming the reservoir assumes a generally triangular shape; the manual pump is located near one of the vertices of this triangle and the filling site near another vertex. During implantation, the pouch can easily be positioned in such a way that the pump shall be in the lower part while the filling site is in the upper part; such a design allows filling by gravity the volume chamber and in the case of air in the reservoir, this design assures that this air shall rise toward the filling site from which it may be purged.

In another feature of the invention, the elastic expulsion membrane is essentially plane when at rest and is impermeably bonded around the recess of the case of a rim provided for that purpose. This design assists in making manufacture cheaper and allows the membrane to intrinsically deform in order to hug the bottom of the recess of the case when a manual pressure is applied.

The diverse constituents of the device of the invention (flexible walls, stiffening frame, injection septum, pump unit, expulsion membrane . . . ) are made from biocompatible materials and examples will be founds further below; the assembly is preferably covered with a thin and flexible coat of a biocompatible substance, in particular silicone, which further enhances impermeability and device biocompatibility.

The expulsion membrane of the pump advantageously is made of an elastic material of the self-sealing type in order to provide the pump with an auxiliary function of being a site of chronic injections. The main drug contained in the reservoir therefore may be injected at will, however the practitioner if necessary still can inject another substance by a mere percutaneous puncture using the device of the invention without being forced to undertake a more delicate injection into the particular body compartment (for instance intravenous, intra-arterial, intra-rachidic, cerebral intraventricular, intrapertioneal injections . . . ). This auxiliary injection site also may be used to inject opaque products for the purpose of checking the impermeability of the pump and of the catheter.

DESCRIPTION OF THE DRAWINGS

Other features, aims and advantages of the invention shall become clearer in relation to the description below and the attached drawings showing a preferred embodiment.

FIG. 4 is a detailed section on an enlarged scale in a plane C (parallel to the plane AA'), FIG. 5 is a detailed section on the same scale as FIG. 4 in a plane D which is parallel to the plane BB', FIG. 6a diagrammatically shows the device implantation in the right lateral position in the abdominal wall of a patient, while

DESCRIPTION OF PREFERRED EMBODIMENTS

Figure 1:
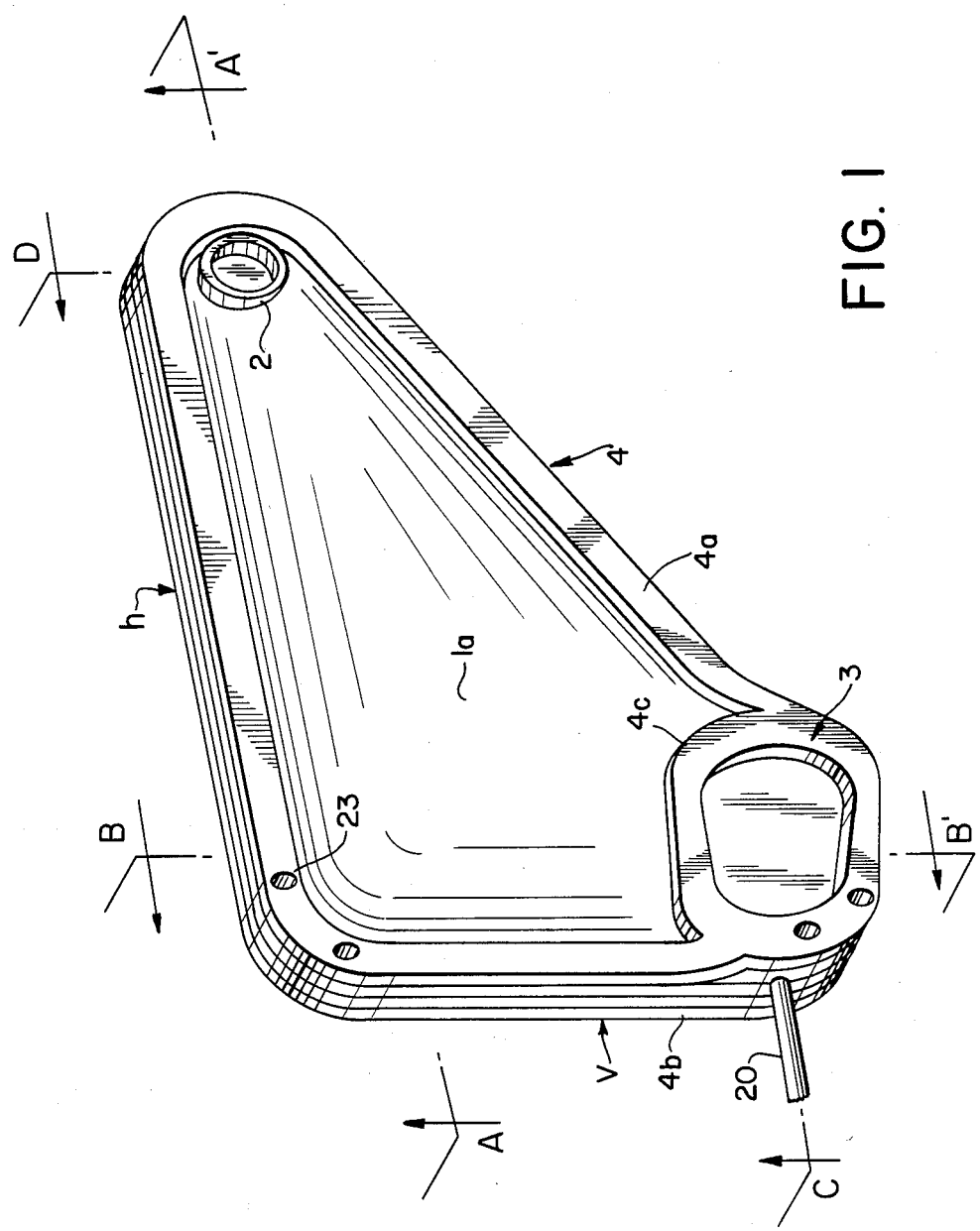
FIG. 1 is a perspective on an enlarged scale of the device of the invention.
Figure 2:
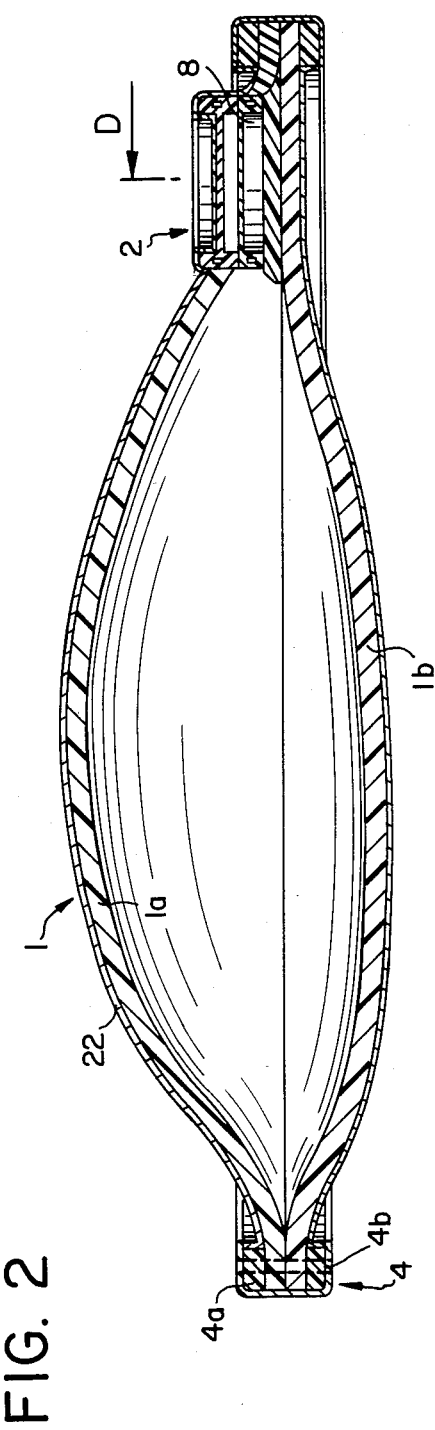
FIG. 2 is a section in a plane AA' parallel to the longitudinal side (h) of the device.
Figure 3:
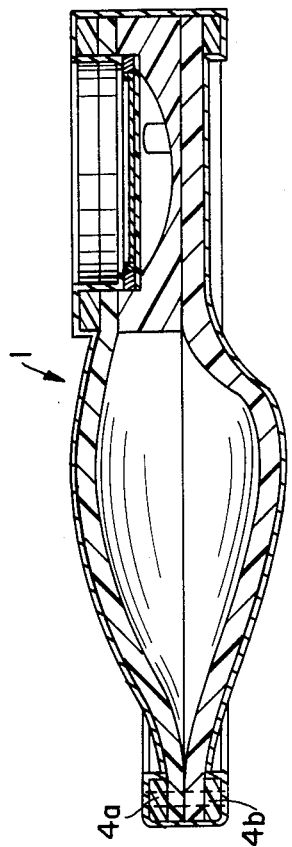
FIG. 3 is a section in a plane BB' parallel to the short side (v) of the device.

The device shown in FIGS. 1 through 5 (on a scale of about 1.75 times natural size in FIGS. 2 and 3 and about 4 times natural size for FIGS. 4 and 5) is intended for implantation in the subcutaneous tissues in order to allow sequential injection by unit steps of a dose of therapeutant (embolus) into a body compartment, for instance an intrarachidic compartment, while being rechargeable by mere percutaneous puncture at the end of its autonomous time.

This device comprises a flexible pouch 1 including two flexible walls 1a and 1b, one of them (1a) being called the external wall and being intended to be aligned near the skin in the course of the implantation, while the other wall (1b), called the internal wall, points toward the internal tissues. Each wall 1a or 1b is preformed and made of a flexible, biocompatible plastic, in particular dacron-reinforced silicone, so as to evince in the rest position the crosssection of a dome, as shown by the Figures. The outer wall 1a curves more than the internal wall 1b which is substantially flatter in order to improve device integration into the tissues.

Seen in topview, these flexible walls assume a generally triangular shape with rounded vertices. In particular these walls are arranged in such a way that the pouch 1 assumes the overall shape of a nearly right triangle, with one side (v) of the right angle being shorter than the other side (h).

These flexible walls 1a and 1b are impermeably bonded to each other along their rims, with a filling site 2 being located in the acute angle subtended by the long side h and the hypothenuse near the corresponding vertex on one hand, and with a manual pump 3 located on the other hand in the acute angle subtended by the short side v and the hypothenuse near the corresponding vertex.

Be it noted that the two walls of the pouch 1 can be joined together when being molded so as to directly achieve an integral pouch.

The flexible pouch 1 made in this manner is stiffened at the rims of its flexible walls by a semi-rigid peripheral frame 4 comprising two elements 4a and 4b which are bonded to each other on the external and internal walls 1a and 1b respectively. The frame is rounded at the angles to follow the shape of the flexible walls and is made of polytetrafluoroethylene so that the pouch shall remain radially flexible while retaining its freedom of deformation perpendicularly to its plane.

The frame element 4a fastened to the external flexible wall 1a is provided with an extension 4c around the pump 3.

When filled, the flexible pouch 1 stiffened by its peripheral frame 4 assumes an asymmetrical doubly convex shape of which the thickness is slight compared to its other dimensions, and is easily inserted into the subcutaneous tissues while adapting itself to the tissues shapes. The capacity of the reservoir it so forms is up to 30 to 50 cm³ without there being any bother to the patient. As a rule an opiate embolus is between 0.4 and 0.6 cm³ whereby the average autonomy of the device easily goes up to 80 to 100 emboli.

The filling site 2 is shown in detail in FIG. 5 and comprises a stiff stop plate 5 bonded on the flexible internal wall 1b and of a ring 6 solidly joined to said plate and bearing an injection septum 7. The flexible external wall 1a includes a window near the ring so that the septum 7 matches this window and is directly accessible; the external wall 1a is impermeably bonded around the ring 6.

The ring 6, its septum 7 and the stop plate 5 bound a filing chamber 8 communicating with the inside volume of the flexible pouch 1 by two holes such as 9 in the ring 6.

In this example, the septum 7 comprises two elastic membranes 7a and 7b separated by a vacuum and joined each to a peripheral bead such as 7c, while the ring 6 comprises two annular elements 6a and 6b forming the core of the peripheral membrane beads 7c.

The stop plate 5 is made of a rigid biocompatible material, in particular a polycarbonate; the membranes 7a and 7b their beads 7c are made of an elastic biocompatible material, in particular self-sealing silicone; the elements 6a and 6b of the ring are made of a rigid biocompatible material, in particular polytetrafluoroethylene.

The membranes 7a and 7b and their beads 7c are molded with insertion of the ring elements 6a and 6b and the assembly is stacked and impermeably bonded to the stop plate 5.

The reservoir comprising the pouch 1 is filled by an injection needle piercing the septum 7 until it makes contact with the plate 5; the liquid injected into the chamber 8 drains through the communicating holes 9 in the flexible pouch 1 until it is filled. The two separate membranes 7a and 7b forming the septum constitute a lock chamber offering excellent impermeability even after numerous piercings.

Obviously the injection septum 7 may assume other designs and in particular it may be made by the molding technique known as "silicone plug".

The manual pump 3 is shown in detail in FIG. 4 and comprises an integrally molded rigid case 10 made of a rigid biocompatible plastic, in particular a polycarbonate or dacron-reinforced silicone or polyetherisulfone; the thickness of this case is about 10 mm less than its other dimensions; seen in topview, it shows an elongated shape symmetrical with the axial plane c shown in FIG. 1, with its peripheral edge rounded over its entire periphery.

The upper and so-called active side of the case slightly slopes with respect to the opposite side, whereby the case becomes thinner away from the reservoir 1.

The case 10 has a shallow recess 11 on its active side, with a depth slight compared to the dimensions of its open cross-section toward the active side.

The depth of this recess 11 increases towards its deeper portion located at the opposite side of the reservoir 1; the recess has a shape matching that of a forefinger: elongated and symmetrical with respect to the plane C and with cross-sections parallel to the active side decreasing in area as they near the recess bottom.

In this example, the central portion of the recess 11 has a conical shape and extends on each side by rounded surfaces to the open cross-section on the active side; this bottom slopes parallel to the plane C toward the deeper part to subtend, within this plane C an angle alpha between 10° and 15° approximately with the active side.

The body side opposite the active side is bonded to the flexible internal side 1b while the active side supports an expulsion membrane 12 sealing the recess 11 in order to bound a volume chamber 13.

At rest the expulsion membrane 12 is essentially plane and slopes the way the active side of the case does toward that side to which the catheter 20 shall be connected; this membrane is fastened by bonding in impermeable manner around the recess 11 on a rim of the body. The membrane 12 is cut to the shape of said rim from a biocompatible plastic, in particular silicone and preferably of the self-sealing type so that it may be pierced by a needle and constitute an injection site. In this example, a retaining ring 14 made of polytetrafluoroethylene is bonded on and at the rim of the membrane 12. Be it borne in mind that just as was the case for the filling site 2, the membrane 12 may be implemented by the "silicone plug" technique.

The flexible wall 1a is provided with a window matching the membrane 12 so as to make this membrane directly accessible; this flexible wall 1a is bonded at the edge of its window on the case 10. The extension 4c of the peripheral frame itself bonded in superposition on the flexible wall 1a forms a harder element allowing to easily locate the membrane 12 by mere touch in order to force it back with the forefinger through the skin of the patient; this action makes it possible to deform the membrane 12 until it hugs the bottom of the recess 11 over its entire surface for the purposes of expelling all of the liquid contained in the volume chamber 13.

In this example the recess 11 has a volume essentially between 0.4 and 0.6 cm$^3$ and in particular of 0.5 cm$^3$ in order to bound together with the expulsion membrane at rest a volume chamber with a capacity of one embolus.

The pump case 10 is provided through its thickness with two mutually opposite ducts 15 and 16 parallel to the sides of the case and issuing on one hand into the recess 11 near its bottom and on the other hand in the peripheral edge of the case and at its outside.

One of the ducts, 15, is located near the flexible pouch so as to issue between the flexible walls 1a and 1b within this pouch. The other duct, 16, which is diametrically opposite to the first, issues outside the pouch on its outer part of the peripheral edge of the case 10.

Each of these ducts has a segment with a larger diameter and issuing along the case periphery (either into the pouch as regards the duct 15 or outside the pouch as regards the duct 16).

The larger segment of the duct 15 houses a safety valve 17 designed to seal the duct if the excess pressure in the flexible pouch 1 exceeds a specific value Pr which in particular is between 20 and 30 millibars.

This valve is of a known type and may consist of a movable ball 17a made of a biocompatible material in particular polytetrafluoroethylene, of a valve seat 17b made of a biocompatible material, in particular silicone, and of a rear stop 17c made of a biocompatible material, in particular polytetrafluoroethylene.

The ball may move slightly (by about 1 mm) and its weight is fitted to allow the liquid to drain from the pouch 1 toward the volume chamber 13 as long as the pressure difference between said pouch and said chamber shall be less than the value Pr and to move toward the seat and seal it when this value is reached or exceeded. Due to the slight axial excursion of the ball, the volume of liquid passing through the duct 15 during the closure process when the pressure limit is reached is very slight (about 0.2 mm$^3$), whereby the increase in volume of the volume chamber 13 (by the upward deformation of the expulsion membrane 12) is very slight.

Obviously, the safety valve 17 may assume any other design known per se.

The larger-diameter segment of the opposite duct 16 houses a one-way, threshold valve 18 fitted to open the duct when the chamber 13 is at an excess pressure higher than a threshold Pc and to seal said duct in the contrary case; this threshold Pc is made equal to or larger than the above mentioned value Pr and in particular is between 50 and 60 millibars.

The valve 18 is located in the duct 16 and rests against a fitting 19 bonded into said duct and to which furthermore is bonded a catheter 20.

This one-way valve may be of the ball and spring type (made of a biocompatible material) such as shown, or any other known type of valve.

Furthermore a check valve 21 which in this instance comprises an elastic tongue bonded to the bottom of the recess so as to mask as necessary the orifice of the duct 15 prevents any liquid from flowing back out of the volume chamber 13 into the reservoir 1.

The chamber 13 fills with liquid through the duct 15, either by gravity or by suction induced by the return of the membrane 12 following its compression. An accidental excess pressure in the reservoir (by involuntary compression of the flexible pouch 1 forming it) in no case can produce a premature injection through the catheter 20. This is so because if this excess pressure remains less than the value Pr, the safety valve 17 remains open but the one-way valve stays closed (Pr<Pc); if this excess pressure becomes larger than Pr, there will begin liquid drainage from the duct 15 (causing a very slight increase in the volume of chamber 13) and the safety valve 17 then closed by the ball 17a coming to rest on its seat 17b, thereby preventing any significant increase in the pressure in the volume chamber (the ball remaining against its seat as long as the excess pressure remains larger than Pr).

A dose is injected by applying pressure to the expulsion membrane 12 (by the operator) until the membrane rests against the bottom of the recess 11 bounding the volume chamber 13; thereupon a high pressure is present in said chamber 13 and causes the one-way valve 18 to open. The check valve 21 prevents any backflow into the reservoir 1.

The outer surface of the device advantageously is covered with a thin, flexible coat 22 in particular of silicone. This coat is deposited after the diverse constituents of the device have been assembled and bonded, by any known process: spraying, dipping .... It improves the device's biocompatibility and increases its impermeability.

Also suture holes such as 23 are present in the rim of the flexible pouch and passing through it, the peripheral frame 4 and the coat 22. These holes are located on one hand near the right angle and on the other hand near the lower angle at the edge of the manual pump 3. In this example there are four holes.

Figure 6A:
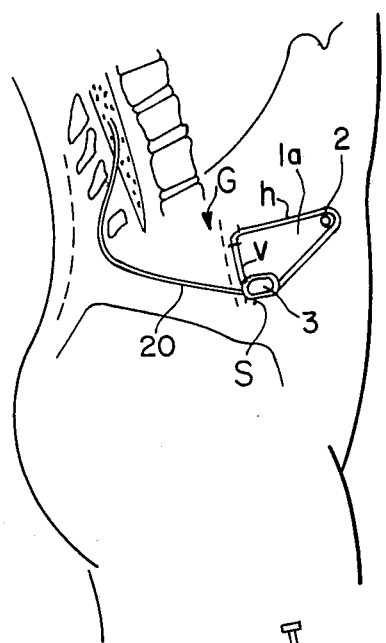
FIGS. 6b, 6c show device in use.
Figure 6B:
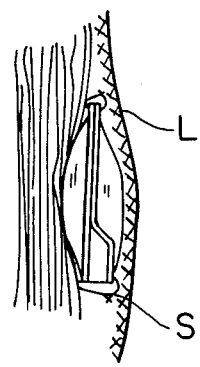
Figure 6C:
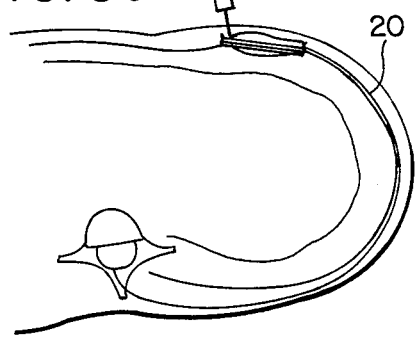

The described device can be implanted as a whole in a subcutaneous zone as illustrated by the FIGS. 6a, 6b and 6c. Illustratively this implantation can take place laterally in the abdominal wall or in the latero-thoracic wall of the patient.

The device relating to FIGS. 1 through 5 is in particular intended to be implanted in the right lateral position. To that end, the triangular flexible pouch 1 has such a geometry that its large side h extends to the right (the implantation site 2 being on the right) when the device is placed in a vertical plane with its short side v vertical and its manual pump 3 in the lower part, and when viewed in elevation at the outer wall 1a.

As shown by FIG. 6a, the device will be implanted after incision along a line G. Its shape allows slipping it easily between the cutaneous line L and the internal musculoaponeurotic tissues M into a subcutaneous pouch fashioned during implantation. Sutures S passing through the holes 23 keep the device perfectly in place; be it noted that the sutures are located on the side of the catheter and eliminate any danger of its twisting where it leaves the device. Furthermore, the device is offset from the incision G and from the suture line closing it, and can be operated (filling, injection) without being hampered by this suture line.

The flexible pouch 1 forming the reservoir is filled with liquid by percutaneous injection through the septum of the filling site 2; this injection is carried out using a suitable needle and corresponds to a volume of liquid which in this example is approximately 80 emboli, whereby the device enjoys substantial autonomy. Be it noted that the reservoir 1 can be filled regardless of the patient's position.

The volume chamber 13 of the manual pump is filled by suction or by gravity, the patient assuming a position such that the pump shall be in the lower part (the patient being up, sitting, or slightly raised above the prone position . . . ).

An embolus is injected by merely pressing on the expulsion membrane through the skin; the operator provides this pressure by his forefinger until he feels the rigid bottom of the pump body; at that time all of the dose has been expelled into the catheter, whereby high-accuracy injections can be performed at will. As discussed above, no danger of accidental injections need be feared at all for instance from the flexible pouch 1 being compressed (if the patient illustratively were lying on his belly). Thus the injection of an embolus takes place accurately with full reliability by a single actuation which is easy to carry out (and where called for by the patient himself).

The presence of an auxiliary access site formed by the pump 3 represents a considerable practical advantage because allowing to inject substances different from that in the reservoir (for purposes of polychemotherapy for instance . . . ).

Be it noted that the arrangement of the device assures that any air bubbles in the reservoir 1 shall automatically rise toward the filling site 2, this air being easily tapable through the septum 7.

Because of the simple design of the device and the absence of mechanical parts (transmitting parts or others), its manufactured cost is much lower than that of the known devices, and it furthermore offers a light weight contributes to reducing patient discomfort. Also, the device is free of any metal part and accordingly the patient may undergo modern imaging exploration without the danger of interference or artifacts.

Figure 7:
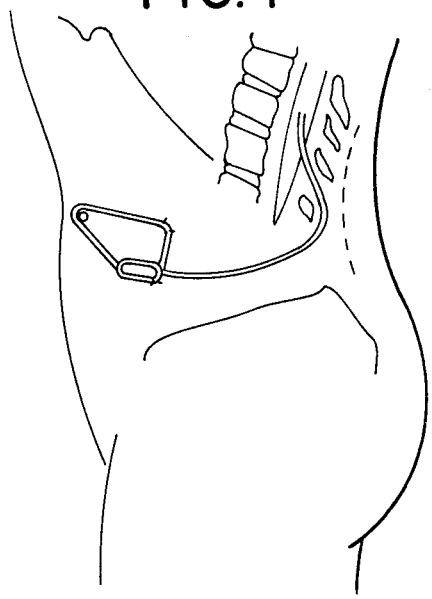
FIG. 7 is a diagram of the implantation of a symmetrical device in the left lateral position of the abdominal wall of a patient.

In the event the implantation shall take place in the later left position the practitioner uses a similar device but symmetrical to the above discussed one as shown in FIG. 7. In this instance the triangular pouch is so arranged geometrically that its large side extends to the left (the implantation site being on the left) when the device is placed in a vertical plane with its small vertical side and with its manual pump in the lower part when viewed in elevation at the outside wall.

I claim:

1. A manually actuated, sequential feed device for implantation in an accessible subcutaneous region for sequentially feeding liquid doses comprising a reservoir (1) having a capacity of plural doses, a filling site (2) for the reservoir and including a filling chamber (8), a septum (7) for injecting a liquid into said chamber and communication means (9) between the filling chamber and the reservoir, and a manual pump (3) having a volume chamber (13) the capacity of which corresponds to one dose, first communication means (15) between the reservoir and said chamber for filling said chamber and second communication means (16) between said volume chamber and an external catheter (20), said reservoir comprising a flexible pouch (1) having a first external wall (1a) and a second, internal wall (1b) opposite said first wall and impermeably bonded to each other along the edges thereof, said manual pump including an integral rigid body (10) having a concave recess (11) opening toward an active side of said body in order to form said volume chamber (13), and placed between said flexible walls (1a, 1b) of said reservoir, said pump further including on its active side an expulsion membrane (12) for sealing the volume chamber and located on the side of the external flexible wall (1a), and fastened by its opposite side to the internal flexible wall, said second communication means including a one-way valve (18) with a pressure threshold designed to open the communication between the chamber and the catheter when the chamber is subjected to an excess pressure higher than a given threshold Pc, said first communication means including a check valve (21) preventing the liquid from flowing back from the chamber into the reservoir, and a safety valve (17) designed to allow gravity draining the reservoir into the volume chamber and closing off the communication if the excess pressure in the reservoir exceeds a value Fr less than or equal to Pc.

2. A feed device as in claim 1 and wherein said pump body (10) is placed between the two flexible walls (1a, 1b) near their rims, and said external flexible wall (1a) includes a window to match said expulsion membrane and is impermeably fastened on said body (10) by the edges of said window.

3. A feed device as in claim 2 and wherein said flexible pouch (1) is stiffened at the edges of the flexible walls (1a, 1b) by a peripheral frame (4) fastened to the edges of said flexible walls.

4. A feed device as in claim 3 and wherein said filling site (2) is located near the edge of the flexible walls (1a, 1b) in a zone of the flexible pouch which is opposite that of the manual pump (3), and said filling site comprises a rigid stop plate (5) fastened on the internal flexible wall (1b) and a ring (6) solidly joined to said plate and bearing the injection septum (7) in such a manner that this septum matches a window of the external flexible wall (1a) fixed impermeably around said ring.

5. A feed device as in claim 3 and wherein said flexible pouch (1) forming the reservoir has a generally triangular shape, and said manual pump (3) is located near one of the vertices and said filling site (2) near another vertex.

6. A feed device as in claim 5 and wherein each flexible wall (1a, 1b) is preformed from a flexible, biocompatible plastic so as to assume the shape of a dome at rest, said peripheral frame (4) including two elements (4a, 4b) made of a biocompatible, semi-rigid plastic fastened in mutually opposite manner respectively on the outer wall (1a) and on the inner wall (1b), and said frame (4) and the rims of the flexible walls (1a, 1b) are rounded off near the angles.

7. A feed device as in claim 6 and wherein said flexible pouch (1) forming the reservoir has the general shape of an approximately right triangle with one side (v) of the right angle being shorter than the other, said manual pump (3) being located in the acute angle subtended by the short side (v) and the hypotenuse near the corresponding vertex, said filling site (2) being located in the acute angle subtended by the long side (h) and the hypotenuse near the corresponding vertex, and a plurality of suture holes (23) in the rim of the flexible pouch near the right angle and near the acute angle adjacent said manual pump (3).

8. A feed device as in claim 7 for implantation in the abdominal wall of a patient in the right lateral position, and wherein said triangular pouch is geometrically designed so that its long side (h) extends to the right when the device is in a vertical plane and with its short side (v) vertical and its manual pump (3) is in the lower part and when viewed in elevation on the side of the external wall (1a).

9. A feed device as in claim 7, for implanation in the abdominal wall of a patient in the left lateral position, and wherein said triangular pouch is geometrically designed so that its long side extends to the left when the device is in a vertical plane with its short side vertical and its manual pump in the lower part and when viewed in elevation from the side of the external wall.

10. A feed device as in claim 6 and wherein said recess (11) of the pump unit is shallow compared with the dimensions of its cross-sectional opening at the active side of said unit, said case (10) being provided around the recess with a rim on which is impermeably fixed the rim of the expulsion membrane (12), and said expulsion membrane when at rest being essentially planar.

11. A feed device as in claim 1 and wherein said recess (11) of the pump has a shape matching that of the forefinger.

12. A feed device as in claim 1 and wherein the active side of the pump body (10) and the expulsion membranes (12) supported by it slope with respect to the opposite side of the unit whereby said unit decreases in thickness toward the catheter (20).

13. A device as in claim 10 and wherein said pump case (10) and its recess (11) have an elongated shape symmetrical with respect to an axial plane.

14. A feed device as in claim 10 and wherein said pump body (10) is integrally molded from a rigid biocompatible plastic and said expulsion membrane (12) is cut to fit the rim of the recess (11) from an elastic biocompatible material.

15. A feed device as in claim 14, and wherein said expulsion membrane (12) is made of an elastic plastic material of the self-sealing type in order to provide the pump with an accessory function of a chronic-injection access site.

16. A feed devices as in claim 14 and wherein said frame element (4a) fixed to the external flexible wall (1a) is provided with an extension (4c) around the pump case (10).

17. A feed device as in claim 10 and wherein said second communication means includes a duct (16) through the case (10) and issuing into the recess (11) near its bottom and into its peripheral edge outside the pouch (1), the end of the catheter (20) being impermeably fastened into said duct, the threshold, one-way valve (18) being housed in said duct (16) and fitted to open it above a threshold pressure Pc approximately between 50 and 60 millibars said second communication means including a duct (15) through the case (10) and issuing into the recess (11) near its bottom and at its peripheral edge between the flexible walls (1a, 1b) bounding the reservoir, the safety valve (17) being housed in said duct (15) and fitted to seal the communication above a pressure Pr essentially between 20 and 30 millibars in the reservoir.

18. A feed device as in claim 10 and wherein the recess (11) has a volume roughly between 0.4 and 0.6 cm$^3$ in order to bound together with the expulsion membrane at rest a volume chamber (13) with a capacity corresponding to one embolus, and wherein the two flexible walls (1, 1b) bound a reservoir with a capacity substantially between 30 and 50 cm$^3$.

19. A feed device as in claim 14, and wherein said injection septum (7) of the filling site comprises two elastic membranes (7a, 7b) supported on the ring (6) so as to be separated by a vacuum.

20. A feed device as in claim 19, and wherein the stop plate (5) of the filling site is made of a rigid biocompatible material, each membrane (7a, 7b) includes a peripheral bead (7c) and comprises an elastic biocompatible material, the ring (6) includes two annular elements (6a, 6b) which form the core of peripheral membrane beads (7c) comprising a rigid biocompatible material.

21. Feed device as in claim 1, characterized by being wholly covered with a thin flexible coat (22) made of a biocompatible material.

* * * * *